United States Patent [19]

Iwaszkiewicz et al.

[11] Patent Number: 4,590,950
[45] Date of Patent: May 27, 1986

[54] ELECTRICAL CONNECTION

[75] Inventors: Jerzy G. Iwaszkiewicz, North Ryde; Janusz Kuxma, Stanmore, both of Australia

[73] Assignee: Telectronics Pty, Limited, Lane Cove, Australia

[21] Appl. No.: 559,239

[22] Filed: Dec. 8, 1983

[30] Foreign Application Priority Data

Dec. 20, 1982 [AU] Australia ............................ 91666/82

[51] Int. Cl.⁴ ................................................ A61N 1/05
[52] U.S. Cl. ................................. 128/786; 128/419 P; 174/75 R; 339/256 S
[58] Field of Search .................. 128/784–786, 128/419 P, 642; 174/74 R, 75 R; 339/256 S

[56] References Cited

U.S. PATENT DOCUMENTS

| | | | |
|---|---|---|---|
| 2,882,514 | 4/1959 | Krantz | 339/256 S |
| 3,348,548 | 10/1967 | Chardack | 128/786 |
| 3,614,296 | 10/1971 | Blomstrand et al. | 339/256 S |
| 3,871,382 | 3/1975 | Mann | 128/419 P |
| 3,995,623 | 12/1976 | Blake et al. | 128/642 |
| 4,258,725 | 3/1981 | O'Neill | 128/419 P |
| 4,280,511 | 7/1981 | O'Neill | 128/784 |
| 4,328,812 | 5/1982 | Ufford | 128/786 |
| 4,444,195 | 4/1984 | Gold | 128/642 |
| 4,458,695 | 7/1984 | Peers-Traventon | 128/786 |
| 4,481,953 | 11/1984 | Gold et al. | 128/786 |

FOREIGN PATENT DOCUMENTS 0085416 8/1983 European Pat. Off. .

Primary Examiner—Lee S. Cohen
Attorney, Agent, or Firm—Finnegan, Henderson, Farabow, Garrett & Dunner

[57] ABSTRACT

An external connection assembly for a conductor insulated by a compressible sleeve. The external conductor is in the form of a ring which is a compressingly fit on to the insulating sleeve and which is so dimensioned with respect to the sleeve that there is no discontinuity in the profile of the sleeve at the ring. Electrical continuity from the conductor to the ring is provided by a bridging wire which passes through the sleeve, the ends of the bridging wire being respectively clamped by compression fit between the conductor and the sleeve, and between the sleeve and the ring.

14 Claims, 8 Drawing Figures

ELECTRICAL CONNECTION

BACKGROUND OF THE INVENTION

1. Field of the Invention

This invention relates to electrical connections and will be described in relation to the use of such connections with leads for cardiac pacemakers. However, it is to be understood that the invention is not limited to pacemaker electrode leads.

2. The Prior Art

Conventional unipolar pacemaker systems consist of a pulse generator and a unipolar pacemaker electrode. In such systems, the return path or indifferent electrode includes the whole or at least a part of the metallic pacemaker case. The drawback of such an arrangement is that the return path of a sensed signal is via tissue fluid and thus subject to interfering signals such as myopotentials. Additionally, electrical activity at the indifferent electrode may give rise to undesirable muscle tissue stimulation or twitching. For these reasons, unipolar pacemakers are usually coated with an insulating layer (such as silicone rubber or paralyne), leaving exposed only a small metal area which is disposed so as to face fatty tissue and thereby act as the indifferent electrode.

A bipolar pacemaker system consists of a bipolar pacemaker connected to a bipolar pacing electrode lead. The bipolar lead has an indifferent electrode incorporated in it which reduces the distance the signal has to travel and minimizes signal interference. In addition, the bipolar pacemaker case is electrically neutral, thus eliminating the problems of muscle twitch and the need for pacemaker coating. These advantages often make the bipolar system the design of choice in pacemaker implants.

A bipolar pacing lead typically consists of a distal electrode tip, commonly made of platinum or platinum-/iridium, and an indifferent ring electrode located a specified distance away from the distal tip. Known bipolar pacing leads have welded or swaged electrode ring constructions, such as that disclosed in U.S. Pat. No. 4,328,812, but which results in a discontinuity in the insulation at the site of the ring. This discontinuity necessitates a relatively complex design at the ring electrode region in order to maintain a seal against ingress of body fluids. The sealing arrangement around the ring, together with the necessity of having a metal supporting insert in the case of a swaged construction, results in a bulky ring assembly and a significantly enlarged lead cross section.

The enlarged ring section makes passage of the lead through the veins of a patient difficult and can also result in thrombus formation. Welded or swaged designs may cause damage to the ring electrode surface during construction thereof, which also increases the possibility of thrombus formation. Welded and particularly swaged electrode ring assemblies also reduce lead flexibility in the area immediately adjacent to the ring.

SUMMARY OF THE INVENTION

It is therefore an object of the present invention to construct a pacemaker lead having a smooth outer profile, continuous insulation and a high degree of flexibility proximate the electrode ring.

It is also an object of the present invention to maintain a uniform cross-sectional dimension in a pacemaker lead to ease passage through the veins of a patient.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the present invention, as embodied and broadly described herein, an electrical connection assembly comprises a first conductor, compressible tubular insulating means surrounding the first conductor, a conductive bridge, one end of which is in electrical contact with the first conductor and the other end of which projects through an aperture in the insulating means, and a second tubular conductor engaged around a predetermined length of the insulating means, the inner periphery of the second conductor being smaller then the outer periphery of the insulating means so that there is a compression fit between the second conductor and the compressible insulating means with the said other end of the conductive bridge being clamped between the insulating means and the second conductor to provide electrical continuity between the first conductor and the second conductor.

In its application to a bipolar pacemaker lead, the first conductor comprises an insulated outer helical conductor and the second conductor is a ring electrode. The electrical contact between the ring electrode and the outer conductor is effected by means of bridging wires which are in contact both with the ring and the conductor and pass through the outer insulator of the lead. The stability of such contact is assured by a friction/compression fit between the electrode ring and the conductor, with the insulator acting as a spring. Thus, the electrical connection does not require a supporting structure and there is no discontinuity in the profile of the outer insulator. The absence of a supporting structure and the use of a compression fit and a continuous insulator are all factors which, in combination, result in a compact, easily manufactured, flexible and smooth profile bipolar pacemaker lead.

The accompanying drawings, which are incorporated in and constitute a part of this specification, illustrate one embodiment of the invention and, together with the description, serve to explain the principles of the invention.

DESCRIPTION OF THE PREFERRED EMBODIMENT

Reference will now be made in detail to the presently preferred embodiment of the invention, an example of which is illustrated in the accompanying drawings.

Figure 1:
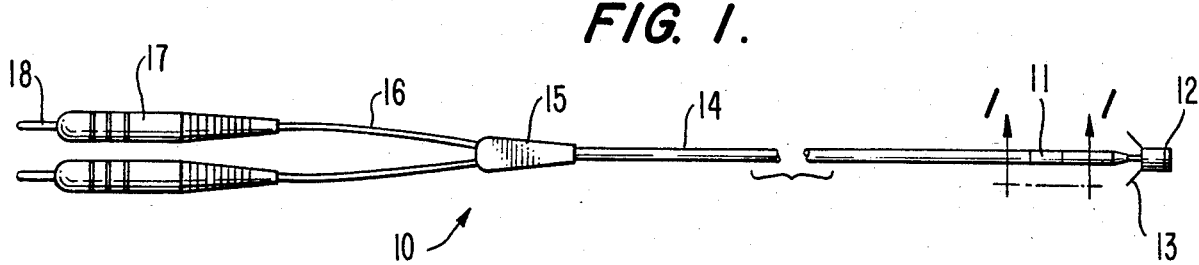
FIG. 1 is a plan view of a bipolar pacing electrode having an electrical connection constructed in accordance with the present invention.

A bipolar pacing lead is shown in FIG. 1 and is generally denoted by the numeral 10. The lead has a ring electrode 11 spaced from a distal electrode tip 12. Tines 13 adjacent electrode tip 12 assist in the placement of the distal electrode in the patient's heart. Extending from both sides of ring electrode 11 is an outer insulation 14 which terminates in a bifurcated protector sleeve 15. Two insulated conductors 16 which emerge from sleeve 15 each has an electrode tip 18 partially covered by a sleeve 17.

The present invention will now be discussed in detail with respect to FIG. 2.

According to the invention, an electrical connection assembly comprises a first conductor. As embodied herein, the first conductor is conductor 19 which may be multi- or uni-filar and made of highly corrosion resistant material such as stainless steel 316L, MP35N, or a combination of either of these with silver in a drawn brazed strand (DBS) configuration. Preferably, the first conductor 19 has a generally cylindrical cross section and may be formed by helically winding a wire conductor, as shown in FIG. 2. However, other shapes may be employed for conductor 19 without departing from the spirit or scope of the present invention.

Also according to the present invention, a compressible tubular insulating means is provided surrounding the first conductor. As embodied herein, the insulating means is outer insulator 14 which surrounds first conductor 19. Outer insulator 14 may be a silicone elastomer, polyurethane elastomer or equivalent compressible insulating material.

In accordance with the invention, a conductive bridge is provided, one end of which is in electrical contact with said first conductor and the other end of which projects through an aperture in said insulating means. As embodied herein, the conductive bridge may comprise a wire 20 of circular cross-sectional dimension, but it may also be of other forms, such as thin foil. In the embodiment illustrated in FIG. 2, the conductive bridge comprises two such wires 20 symmetrically disposed relative a cross section of the lead, i.e. radially spaced an equidistant apart. However, a single wire, or more than two wires, may be employed as a conductive bridge, and with symmetrical or asymmetric spacing, all without departing from the spirit or scope of the present invention.

Figure 2:
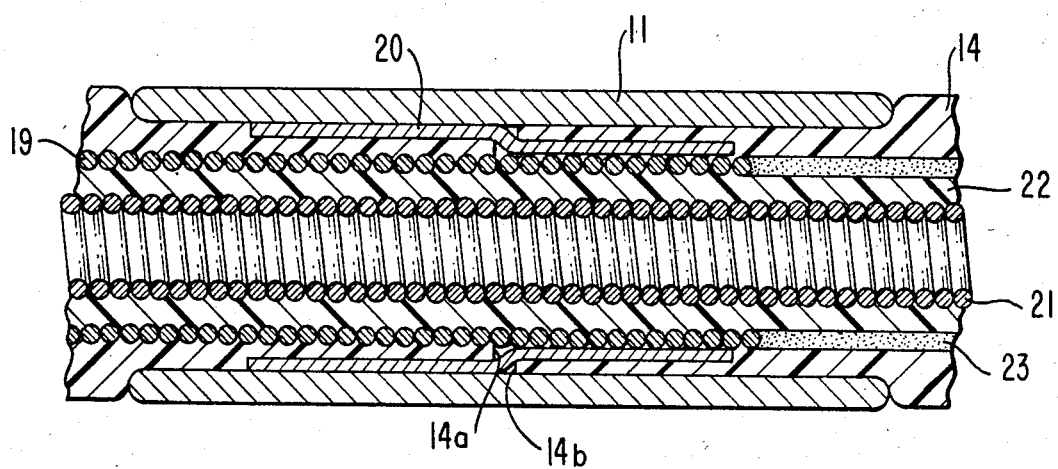
FIG. 2 is an enlarged cross-sectional view of the electrical connection of FIG. 1 taken along lines 1—1.

Wire bridge 20 may be made of platinum or platinum/iridium or similar material, and passes through a small opening in the insulator, shown as 14a, 14b in FIG. 2. As set forth in further detail hereinbelow, the opening defined by 14a, 14b is preferably a small orifice, such as that made by a punch-like operation. Other types of openings, such as elongated slits, may alternately be employed to satisfy, for example, manufacturing requirements without departing from the scope and spirit of the present invention.

According to the invention, a second tubular conductor is provided engaged around a pre-determined length of said insulating means. As embodied herein, the second tubular conductor is ring electrode 11. As described in further detail hereinbelow, ring electrode 11 is fitted over a compressed portion of outer insulator 14 in the vicinity of bridging conductor 20. The diameter of the outer periphery of ring electrode 11 approximates that of outer insulator 14 where in those portions the latter is not compressed, so that when the ring electrode is fitted over the compressed portion of insulator 14, there is no discontinuity in the external shape or profile of the lead proximate ring electrode 11.

By inserting bridging conductor 20 through opening 14a, 14b in outer insulation 14, one end of bridging conductor 20 is thus in electrical contact with first conductor 19. Similarly, by disposing ring electrode 11 on the exterior of outer insulation 14 over the exposed end of bridging conductor 20, the bridging conductor also is in electrical contact with ring electrode 11. This arrangement thus forms the indifferent electrode ring assembly of a bipolar pacing lead.

Ring electrode 11 may be fabricated from platinum, platinum/iridium or any similar material. Preferably, ring electrode 11 is positioned so that opening 14a, 14b is centrally longitudinally disposed relative thereto. Also according to a preferred construction, bridging conductor 20 is positioned so that approximately one-half of its overall length is in contact with ring electrode 11 and one-half is in contact with first conductor 19. It should be appreciated, however, that other placements of ring electrode 11, bridging conductor 20 and opening 14a, 14b are possible without departing from the spirit or scope of the present invention.

Also shown in FIG. 2 is an inner conductor 21 provided within the interior of first conductor 19. Inner conductor 21 is spaced apart from first conductor 19 and insulated therefrom by an inner insulator 22. Like the first conductor, inner conductor 21 can be of a multi- or uni-filar construction using stainless steel 316L, MP35N or DBS. Inner insulator 22 may be made of polyurethane or silicone elastomer or any similar material. The inner insulated conductor 21 may be connected to a distal electrode such as electrode tip 12 shown in FIG. 1.

As shown in FIG. 2, first conductor 19 extends at least as far as the contacting end of bridging conductor 20 and may further extend a distance equivalent to the end of ring electrode 11. Thus, the left-most end (referring to FIG. 2) of first conductor 19 extends towards one of insulated conductors 16 (not shown) to permit electrical connection with auxiliary equipment. In the event first conductor 19 does not extend as far forward, i.e. towards the right in FIG. 2, as inner insulated conductor 21, a gap will be formed between the inner periphery of outer insulator 14 and the outer periphery of inner insulator 22. This gap between the outer and inner insulators can be filled by an adhesive 23 consisting of a silicone or polyurethane elastomer of liquid consistency, or the like.

PREFERRED METHOD OF MANUFACTURE

A presently preferred method of making the electrode ring assembly according to the present invention consists of three stages:

(a) Making the Outer Insulator/Bridging Wire Assembly

Figure 3:
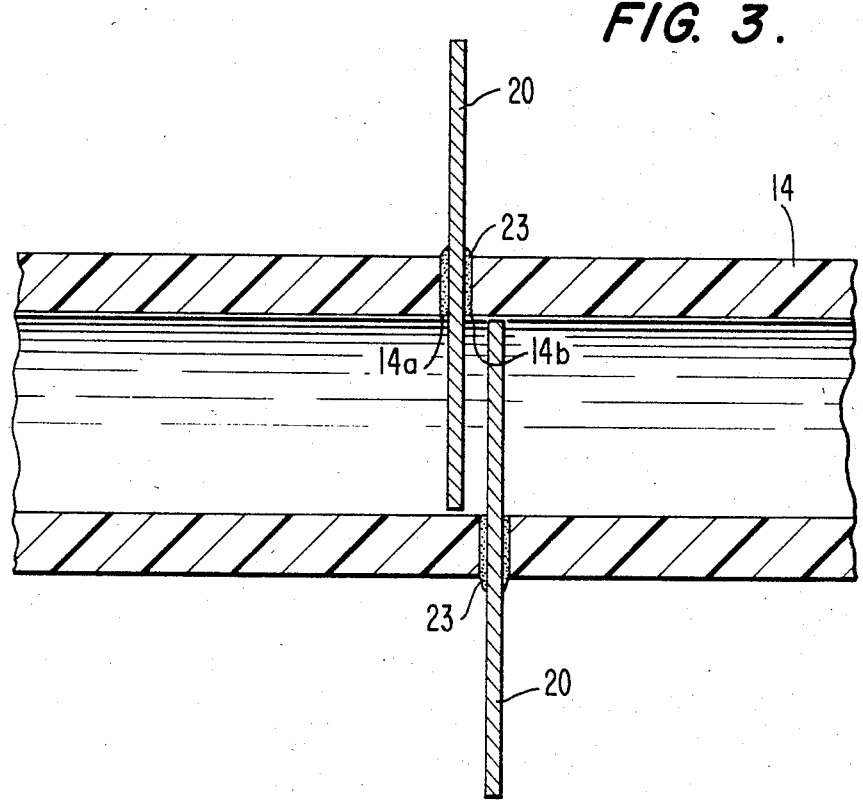
FIG. 3 is a cross-sectional view of the first stage of assembly of the electrical connection shown in FIG. 2.

Referring to FIG. 3, this subassembly is made by piercing a small hole in the insulator 14, which may be a silicone rubber elastomer such as Dow Corning Silastic ® Rx50 tubing of I.D. 1.55, O.D. 2.35, with a platinum/iridium bridging wire 20 that is $50\mu$ to $100\mu$ in diameter (preferably $80\mu$). Wire 20 is then slid into position and cut to length as shown.

Sealing of the opening 14a, 14b around the wire is preferred and may be accomplished by careful application of an adhesive 23 such as Dow Corning Silastic ® A. As shown in the drawing, two wires 20 may be employed as the bridging conductor and are preferably disposed at 180° with respect to each other, i.e. directly opposite one another. For convenience and clarity of illustration, FIG. 3 depicts the wires as being slightly offset with respect to one another. It is thus possible to employ one, two or more than two wires as the bridging conductor without departing from the spirit or scope of the invention. Preferably, such wires are spaced equidistant apart about the first conductor, although other spacing could be used, as desired to aid in ease of manufacturing.

Figure 4:
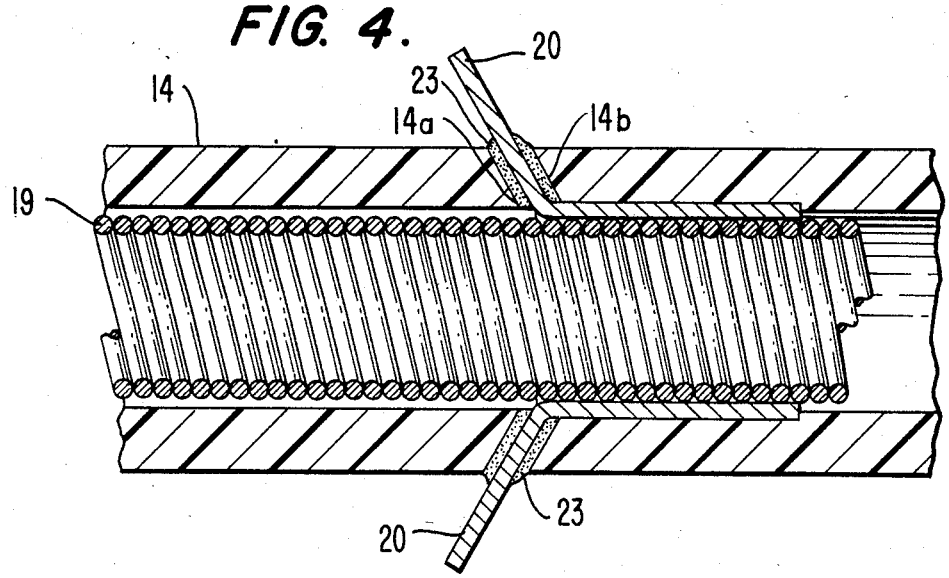
FIG. 4 is a view similar to FIG. 3 showing the second stage of assembly of the electrical connection.

Opening 14a, 14b may be made radially and normal to the longitudinal axis of insulator 14 so that bridging wires 20 are inserted perpendicular to the longitudinal axis, as shown in FIG. 3. Alternately, opening 14a, 14b, and hence wires 20, may be aligned radially, albeit at an obtuse or acute angle to the longitudinal axis of insulator 14. This construction is illustrated in FIG. 4, as explained in further detail hereinbelow. Either arrangement may be employed, as may be convenient or preferable, without departing from the spirit or scope of the present invention.

(b) Outer Conductor/Bridging Wire Assembly

Referring to FIG. 4, this assembly is made by sliding the first conductor 19 coaxially into the interior of the outer insulator having the bridging wire assembly created as described in stage (a) above. Conductor 19 is then advanced carefully so that it assumes the position illustrated in the drawing, simultaneously bending the bridging wires so that ultimately the wires 20 are encaptured by compression and friction between first conductor 19 and outer insulator 14. Bridging wires 20 are thus in electrical contact with first conductor 19. The position of the wires 20 in relation to conductor 19 is preferably controlled so that the wires do not pass beyond the end of the first conductor 19.

It should be appreciated that insertion of first conductor 19 and subsequent bending of wires 20 may deform openings 14a, 14b. That is, if openings 14a, 14b and wires 20 were initially aligned perpendicular to the longitudinal axis of outer insulator 14, as shown in FIG. 3, then insertion of first conductor 19 will deform of the openings into the configuration shown in FIG. 4.

(c) Electrode Ring Assembly

Figure 5A:
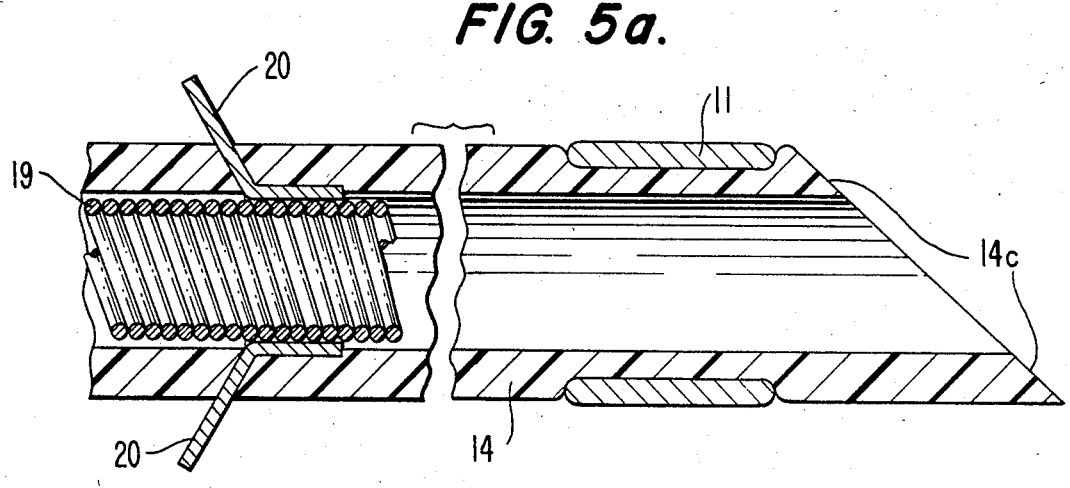
FIGS. 5a to 5c are cross-sectional views of the third stage of assembly of the electrical connection.

As shown in FIG. 5a, a tapered section 14c is next created on the outer insulator 14 portion not supported by the first conductor 19. This taper facilitates positioning electrode ring 11, whose dimensions are typically 1.8−2.0 mm I.D. and 2.3−2.5 mm O.D. (preferably 1.85 mm and 2.5 mm, respectively), and typically 6.2 mm long, over the outer insulator 14, whose outer diameter (typically 2.0−2.5 mm and preferably 2.35 mm with silicon elastomer) is always larger than that of the inner diameter of ring 11. This effects a compression fit will result in the final assembly.

Figure 5B:
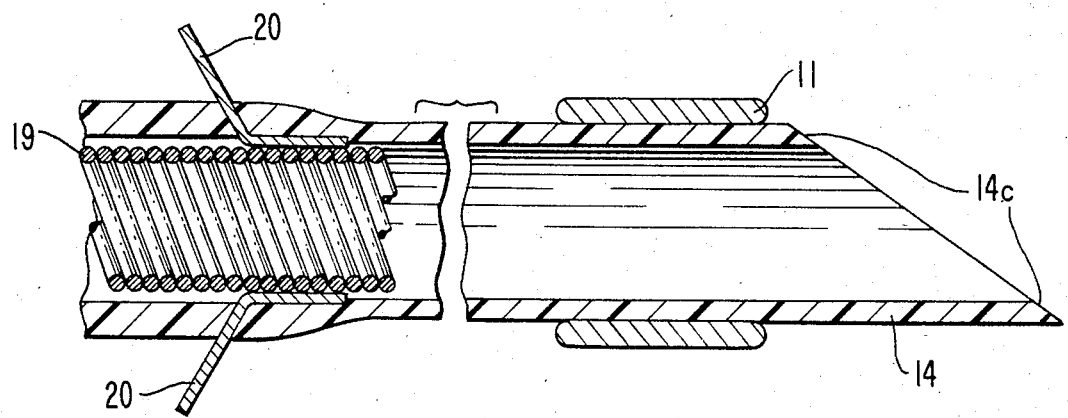

As shown in FIG. 5b, the tapered portion 14c of outer insulator 14 is extended, e.g., stretched, typically 100–200% to reduce its outer diameter. This outer diameter reduction enables the electrode ring 11 (previously in an interference fit) to be advanced without much restraint towards ends of bridging wires 20 protruding from the outer insulator 14.

Figure 5C:
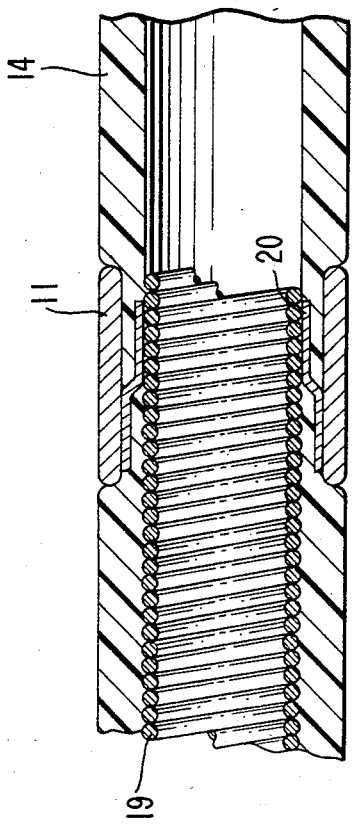

As shown in FIG. 5c, ring 11 is then slipped carefully over bridging wires 20, bending them down into the surface of outer insulator 14, and the ring is ultimately moved into a position whereby the ends of the bridging wires are fully confined within the ring. Finally, outer insulator 14 is relaxed to provide a compression fit between the electrode ring 11 and the first conductor 19. The bridging wires are thus clamped in place between insulator 14 and conductor 19, and in electrical contact with the latter.

The remaining steps in assembling the bipolar pacing lead, such as construction of the inner conductor/inner insulator assembly, proximal and distal tip terminations, etc., are similar to those practiced in connection with prior art unipolar and bipolar pacing leads and need not be discussed here.

The resulting pacemaker lead constructed according to the present invention has a smooth outer profile, has continuous insulation, is easily manufactured and is very flexible in the vicinity of the electrode ring.

Figure 6:
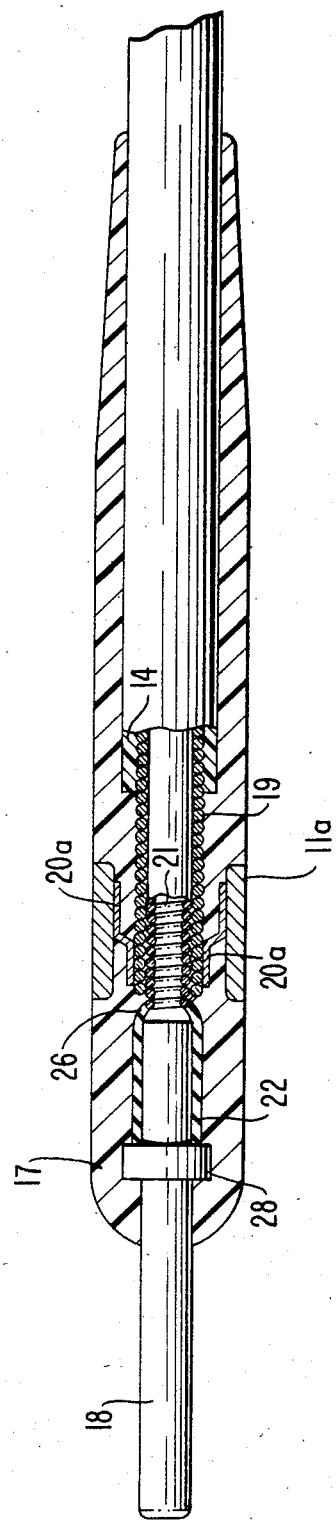
FIG. 6 is a cross-sectional view of an electrical connection according to one embodiment of the invention as applied to the proximal end of a bipolar pacing lead.

An electrical connection according to the invention could be used as a connector for a coaxial bipolar lead/pacemaker connector, as shown in FIG. 6, or as an electrical connector for general application in the electronics or electrical field. In FIG. 6, sleeve 17 encases the proximal end of outer insulator 14 and outer conductor 19. Bridging wires 20a connect the outer conductor 19 to the electrode ring 11a, and the electrode tip 18 is connected to the end of the inner conductor 21. The proximal end of the inner insulator 22 has a bell mouth 26 which engages the inner end of tip 18 and terminates at a shoulder 28 of tip 18.

It will be apparent to those skilled in the art that further variations to both the electrical connection design and the method of making the same can be made without departing from the scope or spirit of the invention. Thus, it is intended that the present invention cover the modifications and variations of this invention provided they come within the scope of the appended claims and their equivalents.

What is claimed is:

1. An electrical connection assembly comprising:
   a first conductor;
   compressible tubular insulating means surrounding said first conductor;
   a conductive bridge, one end of which is in electrical contact with said first conductor and the other end of which projects through an aperture in said insulating means; and
   a second tubular conductor engaged around a predetermined length of said insulating means, the inner diameter of said second conductor being smaller than the outer diameter of said insulating means so that there is a compression fit between said first and second conductors and said compressible insulating means with said insulating means being compressed between said first and second conductors, said one end of said first conductive bridge being clamped between said first conductor and said insulating means, and said other end of said conductive bridge being clamped between said insulating means and said second conductor for providing electrical continuity between said first conductor and said second conductor.

2. An electrical connection assembly according to claim 1 wherein the outer diameter of said insulating means and of said second conductor are substantially similar dimension so that there is no discontinuity in the external shape of the connection assembly.

3. An electrical connection assembly according to claim 1 wherein said first conductor, said insulating means and said second conductor are of substantially cylindrical tubular form, and wherein the inner diameter of said second conductor is smaller than the outer diameter of said insulating means and larger than the outer diameter of said first conductor.

4. An electrical connection assembly according to claim 3 wherein said first conductor projects beyond one end of said second conductor, and an inner conductor is provided within said first conductor and spaced from said first conductor by inner insulating means and which extends beyond both ends of said second conductor.

5. An electrical connection assembly according to claim 4 wherein the space between the inner and outer insulating means beyond said non-projecting end of said first conductor is filled with an adhesive.

6. An electrical connection assembly according to claim 2 wherein said first conductor projects beyond both ends of said second conductor, and an inner conductor is provided within said first conductor and spaced from the first conductor by inner insulating means and which extends beyond both ends of said second connector.

7. An electrical connection assembly according to claim 1 wherein said conductive bridge is a wire and wherein the aperture in said insulating means is sealed around said wire.

8. An electrical connection assembly according to claim 1 wherein said conductive bridge is a wire.

9. An electrical connection assembly according to claim 1 wherein said insulating means includes a second aperture and said conductive bridge includes two wires spaced substantially equidistant apart around the first conductor, each of said wires projecting through a respective one of said apertures in said insulating means.

10. An electrical connection assembly according to claim 1 wherein the aperture in said insulating means is centrally longitudinally located with respect to said second conductor, and said conductive bridge is disposed so that substantially half its length is in contact with said first conductor and half its length is in contact with said second conductor.

11. A body-implantable lead comprising:
an elongated conductor;
a compressible, cylindrical tubular insulating sheath covering said elongated conductor;
a bridging conductor electrical coupled to said elongated conductor and passing through an aperture in said insulating sheath; and
an outer cylindrical, tubular electrode positioned over said sheath in a compression fit with said insulating sheath being compresssed between said elongated conductor and said tubular electrode, said bridging conductor being coupled to said elongated conductor by being compressed between said elongated conductor and said insulating sheath, the portion of said bridging conductor passing through the aperture being clamped between said sheath and said electrode to provide electrical continuity between said elongated conductor and said electrode, the outer diameter of said electrode and said sheath being substantially similar so that there is no discontinuity in the external shape of the lead proximate said electrode.

12. A body-implantable lead according to claim 11 wherein the elongated conductor is of cylindrical, substantially tubular form and terminates proximate one end said electrode, and an inner conductor is disposed within said elongated conductor and spaced therefrom by an insulating sheath.

13. A body-implantable lead according to claim 11 wherein the bridging conductor includes a wire, and the electrode has an inner diameter smaller than the outer diameter of said sheath and larger than the diameter of said elongated conductor so that one end of said wire is firmly clamped between said conductor and said sheath while the other end is firmly clamped between said sheath and said electrode.

14. An electrical lead comprising:
an elongated conductor insulated by a compressible sleeve;
an external tubular conductive connection along a portion of the sleeve, said external connection being compressingly fit on said sleeve and being so dimensioned with respect to said sleeve such that there is no discontinuity in the profile of the lead at the external connection; and
a conductive bridge which passes through said sleeve, and has its ends clamped, respectively, between the conductor and the sleeve and between the sleeve and the external connection by action of the compression fit.

* * * * *